United States Patent [19]

Dumoulin et al.

[11] Patent Number: 5,437,277
[45] Date of Patent: Aug. 1, 1995

[54] INDUCTIVELY COUPLED RF TRACKING SYSTEM FOR USE IN INVASIVE IMAGING OF A LIVING BODY

[75] Inventors: Charles L. Dumoulin, Ballston Lake; Robert D. Darrow, Scotia, both of N.Y.

[73] Assignee: General Electric Comapny, Schenectady, N.Y.

[21] Appl. No.: 194,979

[22] Filed: Feb. 14, 1994

Related U.S. Application Data

[63] Continuation-in-part of Ser. No. 96,205, Jul. 23, 1993, abandoned, which is a continuation of Ser. No. 793,923, Nov. 18, 1991, abandoned.

[51] Int. Cl.$^6$ ...................... A61B 19/00; A61B 19/02
[52] U.S. Cl. ................................. 128/653.1; 128/899; 439/909; 607/154
[58] Field of Search ............... 128/653.1, 653.2, 653.5, 128/899; 439/909; 607/154–156

[56] References Cited

U.S. PATENT DOCUMENTS

| | | | |
|---|---|---|---|
| 4,173,228 | 11/1979 | Van Steenwyk et al. | 128/653.1 |
| 5,005,592 | 4/1991 | Cartmell | 128/899 |
| 5,042,486 | 8/1991 | Pfeiler et al. | 128/653.1 |
| 5,099,845 | 3/1992 | Besz et al. | 128/653.1 |
| 5,271,400 | 12/1993 | Dumoulin et al. | 128/653.5 |
| 5,307,808 | 5/1994 | Dumoulin et al. | 128/653.5 |
| 5,318,025 | 6/1994 | Dumoulin et al. | 128/653.5 |

*Primary Examiner*—Krista M. Pfaffle
*Attorney, Agent, or Firm*—Lawrence P. Zale; Marvin Snyder

[57] ABSTRACT

RF tracking system employs a RF invasive device coupled to surgical tracking equipment for tracking the invasive device. An inductive coupling permits the device to be quickly coupled to, and decoupled from, the equipment. The coupling comprises an inducting coil which transmits a signal from the surgical tracking equipment to a communicating coil in the invasive device. The signal received by the communicating coil passes along leads to a tracked coil in a distal end of the invasive device. The tracked coil transmits the signal as RF energy which is received by the surgical tracking equipment which superimposes the position of the distal end of the invasive device on an X-ray image and displays it on a monitor A sterile shield is employed as a sterile barrier between the inducting coil and the equipment end of the invasive device to prevent contamination of the invasive device by the inducting coil. The cross-section of the invasive device at its equipment end can be made identical to the rest of the invasive device to permit other invasive devices to pass completely over the invasive device.

14 Claims, 3 Drawing Sheets

INDUCTIVELY COUPLED RF TRACKING SYSTEM FOR USE IN INVASIVE IMAGING OF A LIVING BODY

CROSS REFERENCE TO RELATED APPLICATIONS

This application is a continuation-in-part of "INDUCTIVELY COUPLED RF TRACKING SYSTEM FOR USE IN INVASIVE IMAGING OF A LIVING BODY" by C. L. Dumoulin and R. D. Darrow Ser. No. 08/096,205 filed Jul. 23, 1993, now abandoned which was a continuation of "INDUCTIVELY COUPLED RF TRACKING SYSTEM FOR USE IN INVASIVE IMAGING OF A LIVING BODY" by C. L. Dumoulin and R. D. Darrow Ser. No. 07/793,923 filed Nov. 11, 1991, now abandoned. This application is also related to the following Dumoulin et al. applications: "TRACKING SYSTEM TO FOLLOW THE POSITION AND ORIENTATION OF A DEVICE WITH RADIOFREQUENCY FIELDS", Ser. No. 07/753,563; "TRACKING SYSTEM TO FOLLOW THE POSITION AND ORIENTATION OF A DEVICE WITH RADIOFREQUENCY FIELD GRADIENTS", Ser. No. 07/753,565, now U.S. Pat. No. 5,211,165; "STEREOSCOPIC X-RAY FLUOROSCOPY SYSTEM USING RADIOFREQUENCY FIELDS", Ser. No. 07/753,564, now U.S. Pat. No. 5,251,635; "AUTOMATIC GANTRY POSITIONING FOR IMAGING SYSTEMS", Ser. No. 07/753,567, now U.S. Pat. No. 5,255,680; and "MULTI-PLANAR X-RAY FLUOROSCOPY SYSTEM USING RADIOFREQUENCY FIELDS, Ser. No. 07/753,566, now U.S. Pat. No. 5,265,610, all filed Sep. 3, 1991 and assigned to the present assignee. This application is also related to U.S. patent application "INVASIVE SYSTEM EMPLOYING A RADIOFREQUENCY TRACKING SYSTEM" Ser. No. 08/010,720 filed Jan. 29, 1993, a continuation-in-part of filed of "SELF-CONTAINED INVASIVE ASSEMBLIES FOR USE IN RF TRACKING SYSTEMS" Ser. No. 07/793,962 filed Nov. 18, 1991, now abandoned, both by Dumoulin et al. and assigned to the present assignee.

BACKGROUND OF THE INVENTION

1. Field of the Invention

The present invention relates to medical procedures in which an invasive device is inserted into a living body, and more particularly concerns the tracking of such a device with the use of radiofrequency fields.

2. Description of Related Art

X-ray fluoroscopes are used routinely to monitor the placement of invasive devices during diagnostic and therapeutic medical procedures. Conventional X-ray fluoroscopes are designed to minimize X-ray dosage. Nevertheless, some procedures can be very long and the accumulated X-ray dose to the patient can become significant. The long term exposure of the attending medical staff is of even greater concern since they participate in these procedures regularly. Consequently, it is desirable to reduce the X-ray dose during these procedures.

Methods to track an end of an invasive device without the use of X-rays have been disclosed previously in the aforementioned patent applications Ser. Nos. 07/753,563 and 07/753,565, both filed Sep. 3, 1991 hereby incorporated by reference. These applications describe systems in which an invasive device incorporating a radiofrequency coil is placed within the body and its position is followed by broadcasting and detecting a radiofrequency (RF) signal.

Typically a connection between an invasive device and the remainder of a tracking system is made by standard physical connections (e.g. BNC or SMD connectors). Invasive devices such as RF catheters and biopsy needles can be constructed with conventional connectors only if such connector is attached to a invasive device exiting the side of the device, since the interior of the device must be available to provide access for guide wires, contrast media and/or any other object which is part of the procedure. A guide wire, on the other hand, is placed within the body prior to the insertion of a catheter. Since the catheter is placed over the exposed end of the guide wire and since it might need to be changed during the procedure, the guide wire must have a connection whose cross-section is smaller than the catheter. One way to avoid this problem is to make the guide wire very long and place the catheter over the guide wire before it is inserted into the patient. Very long guide wires, however, would be cumbersome to use, and changing the catheter with such a system would necessitate the removal of both the guide wire and catheter.

Another important consideration is the maintenance of a sterile instrument and work area during the procedure. In a typical X-ray angiography procedure, the doctor removes the guide wire every few minutes to sterilize it and to remove any thrombus which might have collected. An exceedingly long catheter or guide wire, or one which is difficult to connect and disconnect, would increase the risk of contamination. The sterility of the equipment to which the catheter and guide wire are attached is also important. Any physical contact of the catheter or guide wire with a non-sterile device requires that the device be either re-sterilized or discarded.

SUMMARY OF THE INVENTION

Invasive devices incorporating RF coils Uued for tracking the device are inductively coupled to a surgical monitoring or tracking system allowing sterile interfaces between the tracking system equipment and the invasive devices. Connections can therefore be easily broken and reestablished, preserving the sterile nature of each invasive device. Inductive coupling of the device to the surgical tracking system equipment is used so that no direct contact between the device and the tracking system is necessary. The connection comprises an inductive coil connected to the surgical tracking equipment. A retaining means holds an equipment end of the invasive device having a communicating coil which communicates with the inductive coil by electrical induction. The invasive device also has an distal end which is inserted into a patient. Leads running the length of the invasive device conduct a signal to the distal end inside the patient. A disposable sterile shield acts as a sterile barrier between the surgical tracking system equipment and the invasive device to prevent contamination. If necessary, the inductively coupled interface between the invasive device and the equipment is constructed with a small cross-section to permit the invasive device to pass through another invasive device in the fashion currently employed in diagnostic radiology.

OBJECTS OF THE INVENTION

It is one object of the present invention to provide an inductively coupled electrical connection to invasive RF devices.

It is another object of the present invention to provide a method of coupling of an invasive device to an external RF system in a manner which maintains a sterile barrier between the device and external system.

It is another object of the present invention to provide a means of rapidly connecting and disconnecting invasive devices to an external system.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings in which:

DETAILED DESCRIPTION OF THE INVENTION

Figure 1:
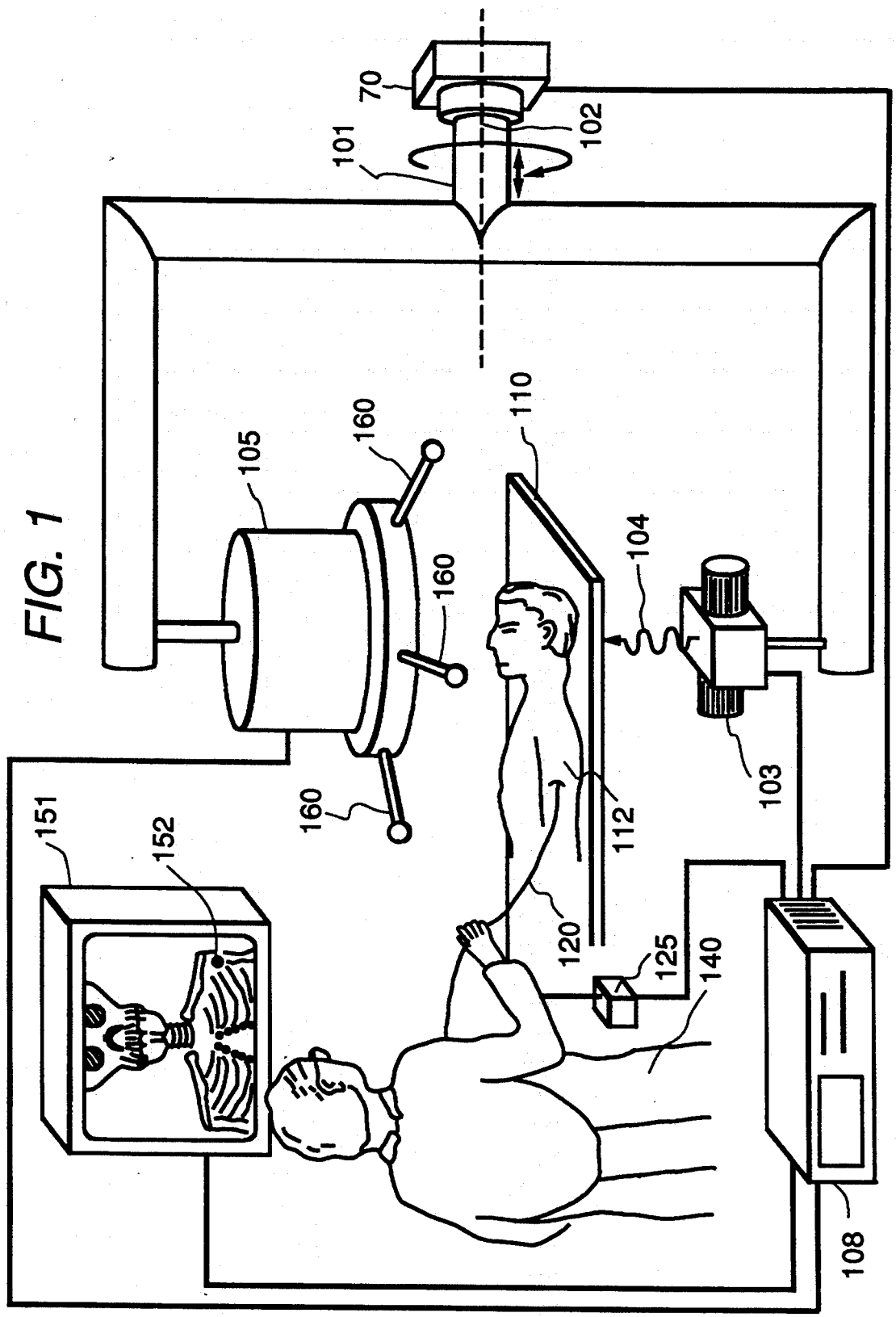
FIG. 1 is a perspective view of one embodiment of the present invention in use during an invasive surgical procedure.

In FIG. 1, a distal end of a invasive device 120 is introduced into a living subject 112 and tracked as described in aforementioned U.S. patent applications Ser. Nos. 07/753,563 and 07/753,565. A support arm 101, capable of being rotated about at least one axis 102 and translated by a gantry control means 70, is provided in order to hold an X-ray source 103 that emits a substantially collimated beam of X-rays 104 suitable for X-ray imaging and X-ray fluoroscopy. Support arm 101 also holds an X-ray detection means 105 aligned with the propagation direction of X-rays 104 emitted by an X-ray source 103. X-rays 104 penetrate a subject support table 110 and subject 112. An invasive device 120 having an distal end is positioned inside the subject by an operator 140. The location of distal end of invasive device 120 is visible as a superimposed image or symbol 152 on an X-ray image of the subject displayed on a display monitor 151. Display monitor 151 is driven by tracking/display unit 108. In fluoroscopic usage, X-ray images are acquired and displayed several (12 to 60) times a second.

The invasive device 120 shown entering the left arm of the subject incorporates at least one small tracked coil (not shown) which is driven by signals propagated from a device interface assembly 125. Tracking/display unit 108 provides power to the tracked coil to create a dipole electromagnetic field which is detected by RF receive coils 160. The tracked coil located in the distal end of invasive device 120 creates a dipole electromagnetic field. This dipole field induces currents and voltages in an array of receive coils 160 distributed around a region of interest. These voltage signals from receive coils 160 are digitized and sent to tracking computer 108 for analysis. Tracking/display unit 108 utilizes non-linear iterative methods to solve several simultaneous equations describing a dipole field to determine the position and orientation of the tracked coil (and therefore the distal end of invasive device 120) as described in patent application Ser. Nos. 07/753,565 and 07/753,563. The calculated position of the distal end of invasive device 120 is displayed by superposition of a symbol 152 on an X-ray image appearing on video monitor 151.

Following the preferred procedure, operator 140 initiates acquisition of an X-ray image only when it is deemed necessary, in order to minimize X-ray dose to subject 112 and operator 140. The instantaneous location of the distal end of invasive device 120 is updated several times per second (ideally 12 to 60 times per second to simulate the motion of conventional fluoroscopy systems) and therefore provides an approximation of the fluoroscopic image of the distal end of invasive device 120 that operator 140 would expect to see with a conventional X-ray fluoroscopic system.

Figure 2:
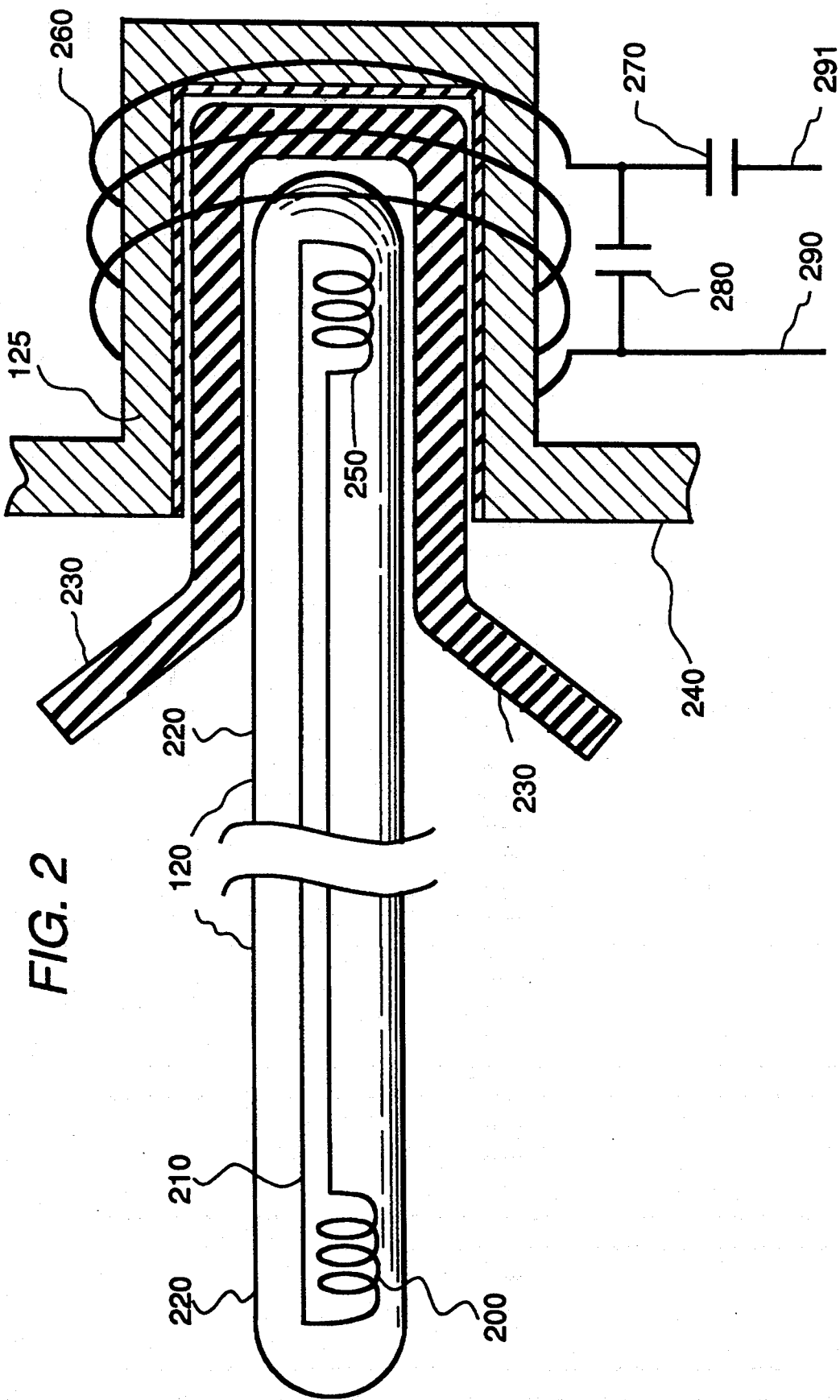
FIG. 2 is a part sectional, part schematic diagram illustrating the inductive coupling between an RF invasive device having an distal end and surgical tracking system equipment for tracking the distal end of the invasive device.

One embodiment of invasive device 120 is shown in greater detail in FIG. 2. The distal end of invasive device is comprised of a tracked coil 200 which is driven by an electrical signal propagated by a pair of conductors 210. This pair of conductors can be arranged either side-by-side, as shown, or coaxially. Tracked coil 200 and conductors 210 are hermetically encased by the exterior surface 220 of the invasive device. The opposite end of the invasive device being the equipment end, is placed in a sterile shield 230 which provides a sterile barrier between the invasive device's exterior surface 220 and exterior surface 240 of interface assembly 125 of the surgical tracking system equipment. In one embodiment of the present invention, sterile shield 230 is constructed of a flexible material which is designed to be impermeable to microbes, such as bacteria or viruses. A common material would be that similar to latex used to construct sterile gloves used in surgery. There are a number of known materials which act as total, or partial, barriers to microbes, especially pathogenic microbes. Sterile shield 230 is designed to encompass the equipment end of invasive device 120, but does not cover the distil end or the intermediate portion between the distil and equipment ends of invasive device 120. It acts to prevent transmission of microbes from physical contact between surgical equipment and invasive device 120.

A communicating coil 250 within the equipment end of invasive device 120 is inductively coupled to an inductive coil 260 which is tuned to the desired radio frequency using the tuning capacitor 280. Sterile shield 230, which is positioned between communicating coil 250 and inductive coil 260, allows inductive coupling through it. Therefore, it is desirable that sterile shield is not a metallic material. Inductive coil 260 is driven by an amplifier (not shown) through conductors 290 and 291. Matching capacitor 270 adjusts the impedance in order to maximize the power transmitted by inductive coil 260. The tracked coil 200 is then tracked as described in patent applications Ser. Nos. 07/753,565 and 07/753,563.

Operator 140 (of FIG. 1) would place sterile shield 230 on the equipment end of invasive device 120. The equipment end of invasive device 120 device is inserted into interface assembly 125 causing sterile shield 230 to envelope the equipment end of invasive device 120. In the preferred embodiment, each time invasive device 120 is removed from interface assembly 125, a new sterile shield 230 is inserted. In an alternative embodiment, the same sterile shield 230 may be used.

In the embodiment of the invention shown in FIG. 2 the equipment end of invasive device 120 which enters the interface assembly 125 has a diameter which does not exceed that of the rest of the invasive device. This permits larger devices to pass circumferential over invasive device 120 when invasive device 120 is detached from interface assembly 125. A further aspect of this embodiment is that RF transmit coil 200 and RF communicating coil 250 inside the invasive device 120 are identically constructed and either end of invasive device 120 may be placed in interface assembly 125. An additional aspect is that the axis of communicating coil 250 is coincident with the axis of the equipment end of the invasive device when coupled to interface assembly 125, thereby maximizing the inductive coupling and permitting rotation of invasive device 120 within interface assembly 125. Axes of transmit coil 200 and inductive coil 260 will be co-linear if the distal end of invasive device 120 is inserted in interface assembly 125.

Several means can be used to insure that invasive device 120 fits securely in interface assembly 125. In the embodiment as shown in FIG. 2, friction between the external surface 220 of invasive device 120 and the sterile shield supported by the external surface 240 of interface assembly 125 holds the equipment end of invasive device 120 in place. Other methods of securing invasive device 120 to interface assembly 125 can include means which make use of suction, magnetic attraction or the like.

The use of this invention can apply to guide wires, catheters, endoscopes, laparoscopes, and other surgical instruments, three-dimensional pointers, and therapeutic devices such as those used for RF ablation therapy.

Figure 3:
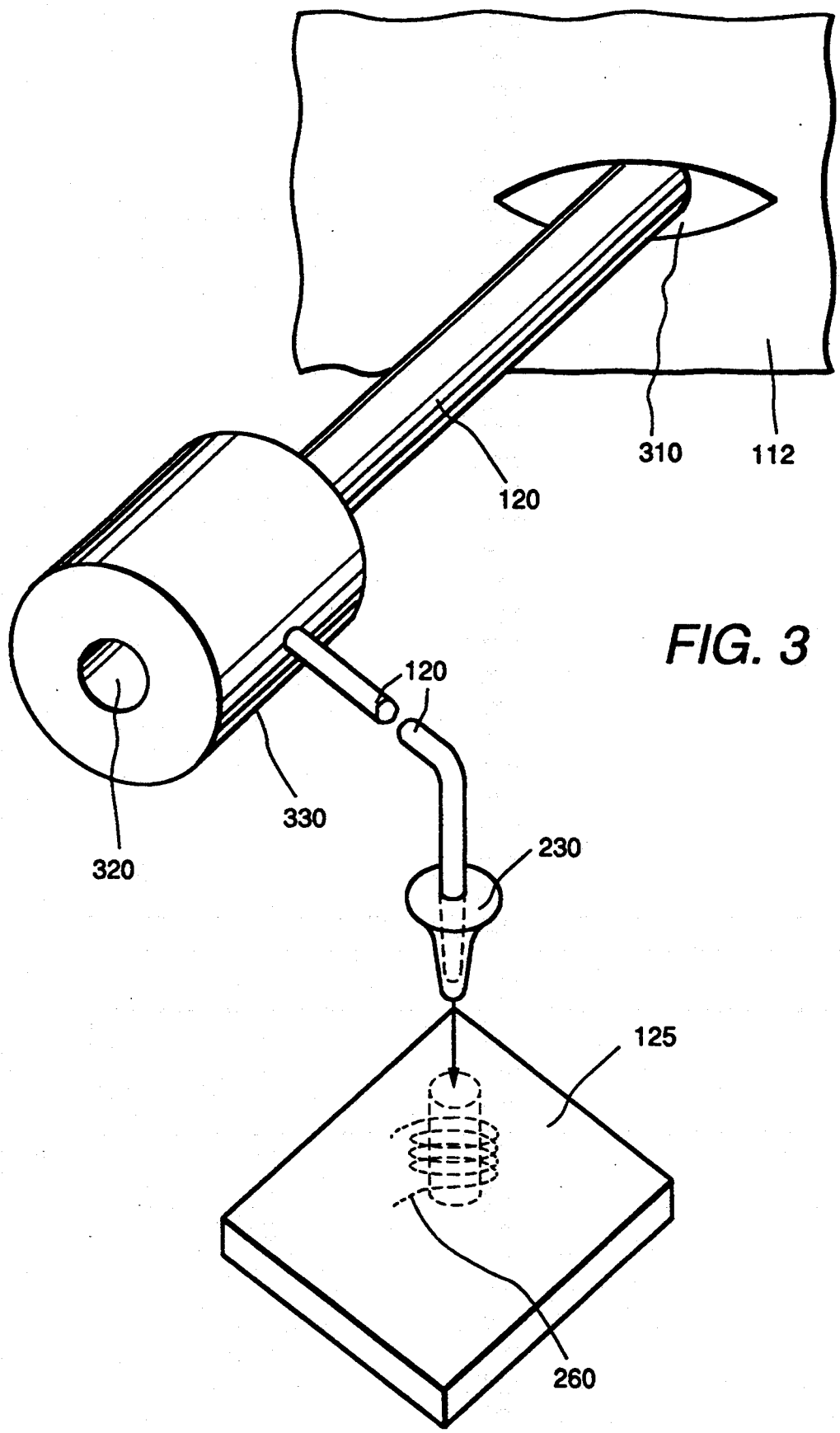
FIG. 3 is a perspective view of an invasive device inserted in a subject having a hollow center for receiving other surgical apparatus.

FIG. 3 shows an embodiment of invasive device 120 inserted through incision 310 of subject 112. A center portion 320 of invasive device 120 is free to accept other surgical equipment. Leads 210, 220 travel from communicating coil 250 through the side of invasive device 120 and collar 330. The leads then pass inside incision 310 through invasive device 120.

In the preferred embodiment of the invention, inductive coil 260 transmits radiofrequency energy which is received by communicating coil 250, passes along leads 210 to tracked coil 200 which radiates the energy. However, reciprocity between transmitters and the receivers exists such that tracked coil 200 may receive energy within the subject 112 of FIG. 1 from coils 160, pass the energy via leads 210 to communicating coil 250 that will transmit RF energy to inductive coil 260, through leads 290 and 291 to tracking/display unit 108.

It may be advantageous to have multiple coil pairs 200, 250 within invasive device 120 to provide additional information to the tracking system. These multiple coils can be either frequency-multiplexed or time-multiplexed by the tracking system. It may also be advantageous to add additional inductors and capacitors to the coils to match and tune the invasive device to selected frequencies.

While several presently preferred embodiments of the novel inductively coupled RF invasive devices have been described in detail herein, many modifications and variations will now become apparent to those skilled in the art. It is, therefore, to be understood that the appended claims are intended to cover all such modifications and variations as fall within the true spirit of the invention.

What is claimed is:

1. A radiofrequency (RF) tracking system to track an invasive device in a living subject comprising:
   a) radiofrequency (RF) source for generating an RF signal;
   b) an interface assembly having
      1. retaining device and
      2. inducting coil connected to the RF source for transmitting the RF signal;
   c) an invasive device having an equipment end held by the retaining device and a distal end intended to be inserted in said subject, the invasive device also having
      1. a communicating coil in the equipment end inductively coupled to the inducting coil receiving the RF signal transmitted by the inducting coil,
      2. electrical leads connected to the communicating coil for passing the received RF signal, and
      3. a transmitting coil in the distal end connected to the electrical leads, for transmitting the RF signal into said subject;
   d) a sterile shield fitting between the interface assembly and the invasive device for creating an antiseptic sterile barrier between the invasive device and the interface assembly;
   e) an RF tracking means for calculating a position of the transmitting coil indicating the location and orientation of the invasive device from the RF signal.

2. The RF tracking system of claim 1, wherein the invasive device comprises one of the group consisting of a guide wire, a catheter, an endoscope, a laparoscope, a biopsy needle and an RF ablation catheter.

3. The RF tracking system of claim 1 wherein the invasive device is constructed with uniform cross-section throughout its length.

4. The RF tracking system of claim 1 wherein the invasive device employs an opening through its length adapted for receiving other invasive devices.

5. The RF tracking system of claim 1 wherein the electrical leads comprise a co-axial cable connected between the communicating coil and the transmitting coil.

6. The RF tracking system of claim 1 wherein an axis of symmetry of the inducting coil and an axis of symmetry of the communicating coil and an axis of symmetry of the equipment end of the invasive device are substantially co-linear.

7. The RF tracking system of claim 1 wherein the retaining device comprises one of the group consisting of friction retention device employing physical friction to retain the invasive device, suction retention device employing a partial vacuum to retain the invasive device and magnetic retention device employing magnetic attraction to retain the invasive device.

8. The RF tracking system of claim 1 wherein the interface assembly further includes a matching capacitor coupled to said inducting coil to tune the inducting coil to a desired radiofrequency.

9. The RF tracking system of claim 1 wherein an axis of symmetry of the inducting coil and an axis of symmetry of the communicating coil are substantially co-linear.

10. A radiofrequency (RF) tracking system to track an invasive device in a living subject comprising:

a) radiofrequency (RF) source for transmitting an RF signal into said subject;
b) an invasive device having an equipment end and a distal end intended to be inserted in said subject, the invasive device also having
   1. receiving coil in the distal end adapted for receiving the RF signal from said RF source;
   2. an electrical leads connected to the receiving coil for passing the received RF signal, and
   3. communicating coil in the equipment end connected to the electrical leads for transmitting the RF signal;
c) an interface assembly having
   1. retaining device for retaining the equipment end of the invasive device, and
   2. inducting coil inductively coupled to the communicating coil for receiving the RF signal transmitted by the communicating coil;
d) a sterile shield fitting between the interface assembly and the invasive device creating an antiseptic sterile barrier between the invasive device and the interface assembly;
e) an RF tracking means coupled to the inducting coil for calculating a position of the receiving coil indicating the location and orientation of the invasive device from the received RF signal.

11. An antiseptic electrical connection for passing a signal between a non-antiseptic set of leads and an antiseptic set of electrical leads in a sterile environment comprising:

a) an interface assembly having
   1. retaining device, and
   2. inducting coil connected to the non-antiseptic set of leads;
b) a sterile housing held by the retaining device having a communicating coil connected to said set of antiseptic leads being inductively coupled to the inducting coil for communicating said signal with the inducting coil;
c) a sterile shield fitting between the sterile housing and the interface assembly creating an antiseptic sterile barrier between the sterile housing, the antiseptic leads, and the interface assembly and non-antiseptic leads.

12. The electrical connection of claim 11 wherein the retaining device comprises one of the group consisting of friction retention device employing physical friction to retain the sterile housing, suction retention device employing a partial vacuum to retain the sterile housing and magnetic retention device employing magnetic attraction to retain the sterile housing.

13. The antiseptic electrical connection of claim 11 wherein the interface assembly further includes a matching capacitor coupled to said inducting coil to tune the inducting coil to a desired radiofrequency.

14. The electrical connection of claim 11 wherein an axis of symmetry of the inducting coil and an axis of symmetry of the communicating coil are substantially co-linear.

* * * * *